United States Patent [19]

Shimoyamada et al.

[11] Patent Number: 4,724,961

[45] Date of Patent: Feb. 16, 1988

[54] SEALABLE CONTAINER READILY UNSEALABLE SEALED PACKAGE CONTAINING A STERILE COMMODITY, AND METHODS OF PRODUCING THE SAME

[75] Inventors: Masahiro Shimoyamada; Sumiyuki Yamakawa, both of Tokyo, Japan

[73] Assignee: Dai Nippon Insatsu Kabushiki Kaisha, Japan

[21] Appl. No.: 879,511

[22] Filed: Jun. 27, 1986

Related U.S. Application Data

[63] Continuation of Ser. No. 613,095, May 22, 1984, abandoned.

[30] Foreign Application Priority Data

May 30, 1983 [JP] Japan .................................. 58-95324

[51] Int. Cl.⁴ .............................................. B65D 73/00
[52] U.S. Cl. ..................... 206/439; 206/484; 206/484.1; 156/272.6
[58] Field of Search ................. 206/439, 484.1, 484; 156/272.6, 272.2, 275.5

[56] References Cited

U.S. PATENT DOCUMENTS

| | | | |
|---|---|---|---|
| 3,554,828 | 1/1971 | Schmedding et al. | 156/272.6 |
| 3,648,834 | 3/1972 | Gifford et al. | 156/272.6 |
| 3,676,249 | 7/1972 | Lemelson | 156/272.6 |
| 3,761,013 | 9/1973 | Schuster | 206/439 |
| 3,819,106 | 6/1974 | Schuster | 206/439 |
| 4,270,658 | 6/1981 | Schuster | 206/439 |
| 4,367,816 | 1/1983 | Wilkes | 206/439 |
| 4,380,485 | 4/1983 | Schuster | 206/439 |

Primary Examiner—Joseph Man-Fu Moy
Attorney, Agent, or Firm—Parkhurst & Oliff

[57] ABSTRACT

A container comprises a first and second wall parts to be heat bonded together along respective sealing portions from thermoplastic resin layers having a polyethylene chain, at least one wall part being a laminated structure comprising a thermoplastic resin inner wall layer with a plurality of minute holes and a paper outer wall layer which is permeable to gases but is impervious to microorganisms, at least one thermoplastic layer of a sealing portion, prior to being heat bonded, being irradiated with ionizing radiation rays to introduce thereinto a crosslinked structure. By seal packaging a medical supply commodity with this container and sterilizing the same with a gas or steam, a readily unsealable, sealed package can be produced for ready use at any time and place.

10 Claims, 5 Drawing Figures

SEALABLE CONTAINER READILY UNSEALABLE SEALED PACKAGE CONTAINING A STERILE COMMODITY, AND METHODS OF PRODUCING THE SAME

This is a continuation of application Ser. No. 613,095, filed May 22, 1984, now abandoned.

BACKGROUND OF THE INVENTION

This invention relates generally to packaging and packaging containers and more particularly to packaging structures particularly suitable for packaging in sealed state tools and instruments for medical treatment such as hypodermic syringes, hypodermic needles, surgical scalpels and scissors, and catheters.

More specifically, the invention concerns packaging structures (hereinafter referred to as "container structures" or simply "containers") which can be subjected to gas sterilization treatment with gases, principally ethylene oxide, steam, and the like to simultaneously sterilize the container and also its contents and, furthermore, when used for packaging an article such as a medical instrument, can be readily unsealed for taking out the article, and which, moreover, can be thus unsealed to produce an unsealed access opening which is in a neatly opened state. The invention further relates to a readily unsealable sealed package comprising a commodity and the container containing the commodity in sealed and sterilized state and to methods of producing the container and the sealed and sterilized package.

Tools and instruments for medical treatment, most of which are intended to be disposable after a single use as a premise in modern medical practice, are packaged with paper impervious to microorganisms and then subjected to sterilization processing with a gas such as ethylene oxide gas or steam. Alternatively, these articles are packaged in containers of synthetic resin film and subjected to sterilization processing with inoizing radiation rays such as gamma rays or electron rays. Thus, the sealed articles can be maintained in a sterile state until they are to be used.

The above mentioned sterilization treatments are generally employed. While the method of sterilization with ionization radiation rays exhibits excellent sterilization efficiency, it requires complicated equipment and is expensive. For this reason, the most generally utilized method at present is that of gas sterilization. Accordingly, in order that gas sterilization, which is the most general sterilization method for packages of medical supplies, will become possible, the most desirable packaging material is a paper of having a characteristic such that it will pass gases therethrough but will not pass microorganisms therethrough. In actual practice, such a paper material is most widely used at present.

A packaging container made of such paper generally has sealing parts on which thermoplastic synthetic resin layers are formed to be mutually heat bonded together at the time of packaging and sealing to form a tight seal. When this seal is to be broken or unsealed, the most commonly used procedure is to pull apart and tear the sealed part. Not only is this procedure difficult, but the tearing occurs, not between the thermoplastic resin layers which participated in the forming of the sealed part, but at the inner parts of the paper layer where the bonding strength is weak. For this reason, paper dust called paper fluff or fuzz is scattered toward the surroundings and adheres to the medical commodity, which has been sealed up to that time. This is not only unsanitary but also gives rise to problems such as the risk of the paper dust infiltrating into the bodies of patients to be treated with the medical commodity.

SUMMARY OF THE INVENTION

This invention seeks to provide principally a package container which can be gas sterilized with gases such as ethylene oxide gas or steam and moreover can be easily unsealed by hand for taking out the contents such as medical supplies by drawing apart first and second wall parts to separate respective sealing parts thereof forming the sealed joint therebetween in a manner to leave a clean and neat unsealed opening.

According to this invention in one aspect thereof, briefly summarized, there is provided a container structure for packaging a commodity in sterile sealed state to produce a readily unsealable sealed package of the commodity, said container structure comprising a first wall part and a second wall part to be heat bonded together along respective sealing parts which are formed from thermoplastic resin layers having a polyethylene chain, at least one wall part of the first and second wall parts being a laminated multilayer structure comprising a thermoplastic resin inner wall layer provided with numerous minute through holes and a paper outer wall layer laminated to the inner wall layer and having the characteristic of being permeable to gases but being impervious to microorganisms, the thermoplastic resin layer of at least one of said sealing parts being subjected, prior to being heat bonded, to irradiation with ionizing radiation rays thereby to introduce thereinto a cross-linked structure.

According to this invention in another aspect thereof, there is further provided a readily unseable sealed package comprising a commodity in a sterile state and a container structure as defined above containing the commodity in a sterile sealed state until it is to be used, the sealed package being easily opened and unsealed at any desired time and place to obtain a clean and neat access opening.

According to this invention in a further aspect thereof, there are provided a method of producing a container structure as defined above and a method of producing a readily unsealable sealed and sterilized package of a commodity as defined above.

The nature, utility, and further features of this invention will become clear from the following detailed description with respect to preferred embodiments of the invention when read in conjunction with the accompanying drawings, briefly described below.

DETAILED DESCRIPTION OF THE INVENTION

Figure 1:
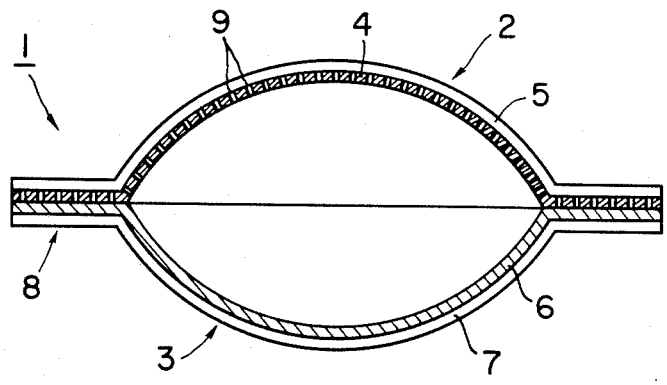
FIG. 1 is a sectional view of one example of a contained structure of bag shape according to this invention.

Referring first to FIG. 1, one example of a readily unsealable container for medical use of bag shape according to this invention is shown therein. This container 1 has a first wall part 2 and a second wall part 3 (upper and lower wall parts as viewed in FIG. 1). The first wall part 2 is a laminated structure comprising an inner wall layer 4 made of a thermoplastic synthetic resin having a polyethylene chain and an outer wall layer 5 of paper. The second wall part 3 similarly is a laminated structure comprising an inner wall layer 6 made of thermoplastic synthetic resin having a polyethylene chain and an outer base layer 7 made of a material not limited to paper.

The thermoplastic resin layer 4 of the first wall part 2 along its outer edge part and the thermoplastic resin layer 6 of the second wall part 3 are in mutually superposed state and form a sealed part 8. Of these two thermoplastic resin layers 4 and 6, at least one layer is formed from a thermoplastic resin having a polyethylene chain into which a crosslinked structure has been introduced by an irradiation treatment with ionizing radiation prior to the formation of the sealed part 8 by heat adhesion means.

In the example now being described with reference to FIG. 1, the above mentioned inner wall layer 4, made of a thermoplastic synthetic resin, of the first wall part 2 is provided with a large number of minute through holes or perforations 9 formed mechanically therethrough by means, for example, of a heated needle or needles. The outer wall layer 5 is a paper layer which is permeable to gases but is impervious to microorganisms. Alternatively, only the second wall part 3 may, of course, have a similar construction wherein the inner wall layer 6 made of a thermoplastic resin and provided with a large number of minute holes 9 is laminated with the outer wall layer 7 made of a paper permeable to gases but impervious to microorganisms. In still another possible arrangement, both the first and second wall parts 2 and 3 may have the above described construction. That is, the only requirement is that at least one wall part 2 or 3 has this construction.

Figure 2:
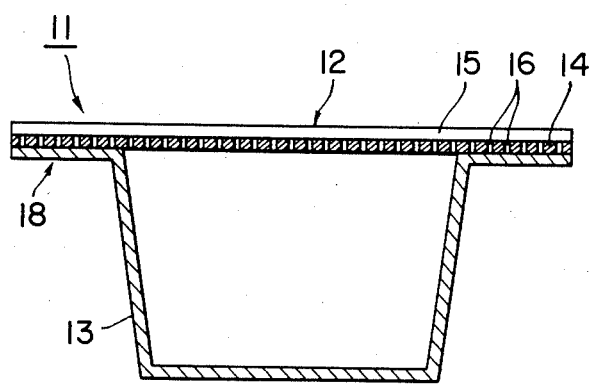
FIG. 2 is a sectional view of another example of a container structure of box-container shape according to the invention.

In another embodiment of this invention as shown in sectional view in FIG. 2, the container is in the form of a box container 11 having a second lower wall part 13 having the shape of a box with an open top and a first upper wall part 12 constituting a lid covering and closing the open top of the lower wall part 13. The upper wall part 12 comprises an inner wall layer 14 which is made of a thermoplastic synthetic resin having a polyethylene chain and is provided with a large number of minute holes 16 and a paper layer 15 laminated with the inner wall layer 14 and being permeable to gases but impervious to microorganisms. On the other hand, the lower wall part 13 is made up of only a sheet of a thermoplastic synthetic resin having a polyethylene chain.

The upper wall part 12 rests on outwardly extending flange parts of the lower wall part 13 at the upper open rim thereof and, at the time of sealing, is heat bonded to the flange parts to form a sealed part 18 similarly to the sealed part 8 in the preceding example shown in FIG. 1.

In most cases, in the container of the above described construction, the thermoplastic resin layer in the laminated material utilized is formed from a thermoplastic resin having a polyethylene chain into which a crosslinked structure formed by irradiation with ionizing radiation rays has been introduced. In such a case, the laminated material is obtained in the following manner. Minute holes or perforations are formed in a film which has been formed from a thermoplastic resin having a polyethylene chain. Thereafter this film is bonded laminately to a paper which will pass gases but will not pass microorganisms. The film is then irradiated with ionizing radiation rays to introduce thereinto a cross-linked structure. Alternatively, minute holes are formed in a film formed from a thermoplastic resin having a polyethylene chain, and this film is then irradiated with the ionizing radiation rays and thereafter bonded laminately with the paper which is permeable to gases but impervious to microorganisms.

Particularly in the case where the laminated material is prepared by the latter procedure, since the heat bondability of the thermoplastic resin film is poor, it is preferable to form an adhesive layer of vinyl acetate, an ionomer, or the like on the paper surface and then to bond together the paper and the resin film. In this case, however, it is necessary to form the adhesive layer, not over the entire surface of the paper, but in a thin state of an order which is almost uneven so as to prevent deterioration of the gas permeability possessed by the paper due to the adhesive layer.

Furthermore, in the readily unsealable container of this invention, the thermoplastic layers used in the formation of the sealed part 8 or 18 comprising mutually heat bonded parts of the thermoplastic resin layers are formed from thermoplastic resins having a polyethylene chain and having the characteristic of assuming a cross-linked structure introduced thereinto upon irradiation thereof with electron rays. Examples of such resins are: polyethylenes such as low-density polyethylene, medium-density polyethylene, high-density polyethylene, and linear low-density polyethylene; ethylene copolymers such as ethylene-vinyl acetate copolymers (saponified substances), ethylene-carboxylic acid copolymers, ethylene-$\alpha$-olefin copolymers, and polypropylene ionomers; polyvinyl chloride; and polystyrenes.

Certain quantities must be considered in the production of the containers of this invention. One quantity is the degree of crosslinking due to irradiation with an ionizing radiation ray introduced into at least one of the thermoplastic resins having a polyethylene chain used to form the sealed part 8 or 18 comprising mutually heat bonded parts of the resins. Another quantity is the quantity of irradiation with the ionizing radiation to which the resin layer is subjected. Such quantities differ with factors such as the size of the container, the weight of the article to be sealed within the container, the heat bonding conditions at the time of formation of the sealed part 8 or 18, and the kind of resin used in the other resin layer used for forming the sealed part 8 or 18 in the container. The pertinent quantities are preferably so selected that heat bonding strength of the sealed part in a container ordinarily obtained will become of the order of 300 to 1,500 grams/15 mm, and ordinarily irradiation with radiation rays of the order of 0.1 to 20 Mrad is preferable.

For the paper layer to be used in the above described manner, high-quality paper, kraft paper, sterile paper, and some others can be used. Furthermore, for the base layer 7, which is not limited to paper, a sheet material such as a metal sheet such as an aluminum sheet, a nylon sheet, a polyethylene sheet, a polypropylene sheet, or a polyethyleneterephthalate sheet can be used, singly or in laminated combinations thereof.

The aforementioned fine holes or perforations 9 or 16 in the resin layer are of a size which will permit the passage therethrough of a gas for sterilization processing. Ordinarily these holes are formed by means of heated needles and are satisfactory if they are generally of diameters of the order of 0.1 to 5 mm formed with a hole forming rate of the order of 10 to 70 percent.

While the container of this invention is of a multilayer construction as described above, it will be obvious that all wall parts are constituted by materials which will not permit passage therethrough of microorganisms.

Furthermore, the sealed part 8 or 18 in the container of this invention is a part formed by mutual heat bonding of thermoplastic resin layers, in which the irradiation with ionizing radiation rays introduced into the resin layers participates. It is sufficient to apply this irradiation treatment to at least the sealing part only, and it need not be applied to all parts.

With regard to the heat bond strength of the sealed part formed by heat adhesion in the sealed package of this invention, the relationships between the heat bond strength, the quantity of irradiation with the ionizing radiation rays, and the heat bonding temperature will now be described with respect to certain examples of composition and construction with reference to FIGS. 3, 4, and 5.

Figure 3:
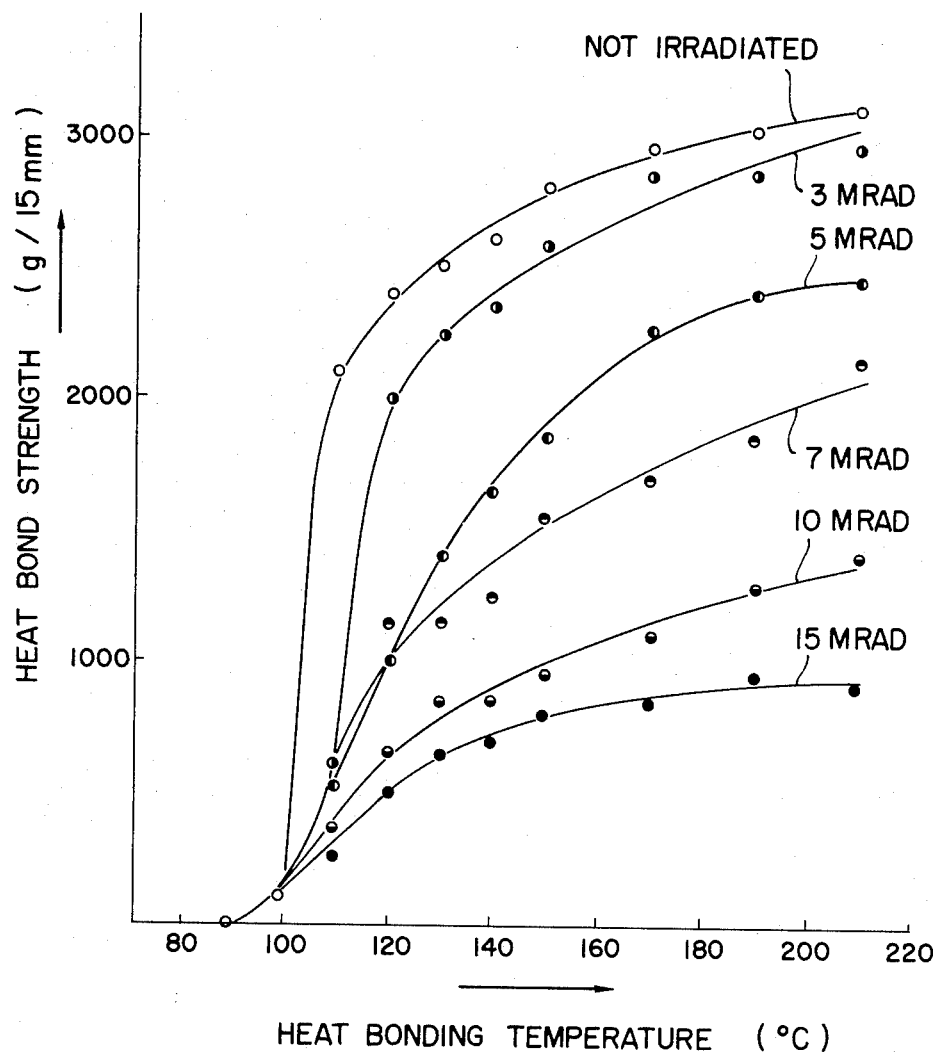
FIGS. 3, 4, and 5 are graphs indicating relationships between heat bonding temperature used in heat bonding a container structure of this invention, the quantity of irradiation with ionizing radiation rays of sealing parts, and the resulting heat bond strength, respectively, for three different conditions of container construction and irradiation of the sealing parts thereof.

FIG. 3 indicates the above mentioned relationships of the sealed part of a sealed package produced by bonding together with an adhesive a polyethyleneterephthalate film of 12-micron thickness and a low-density polyethylene film of 40-micron film to form a laminated film, forming a bag container from this laminated film with the low-density polyethylene film on the inner side, and forming the sealed part 8. Prior to the last step of forming the sealed part, of the two layers of low-density polyethylene film directly related to the formation of the sealed part 8, only the layer on one side was subjected to irradiation with ionizing radiation rays.

Figure 4:
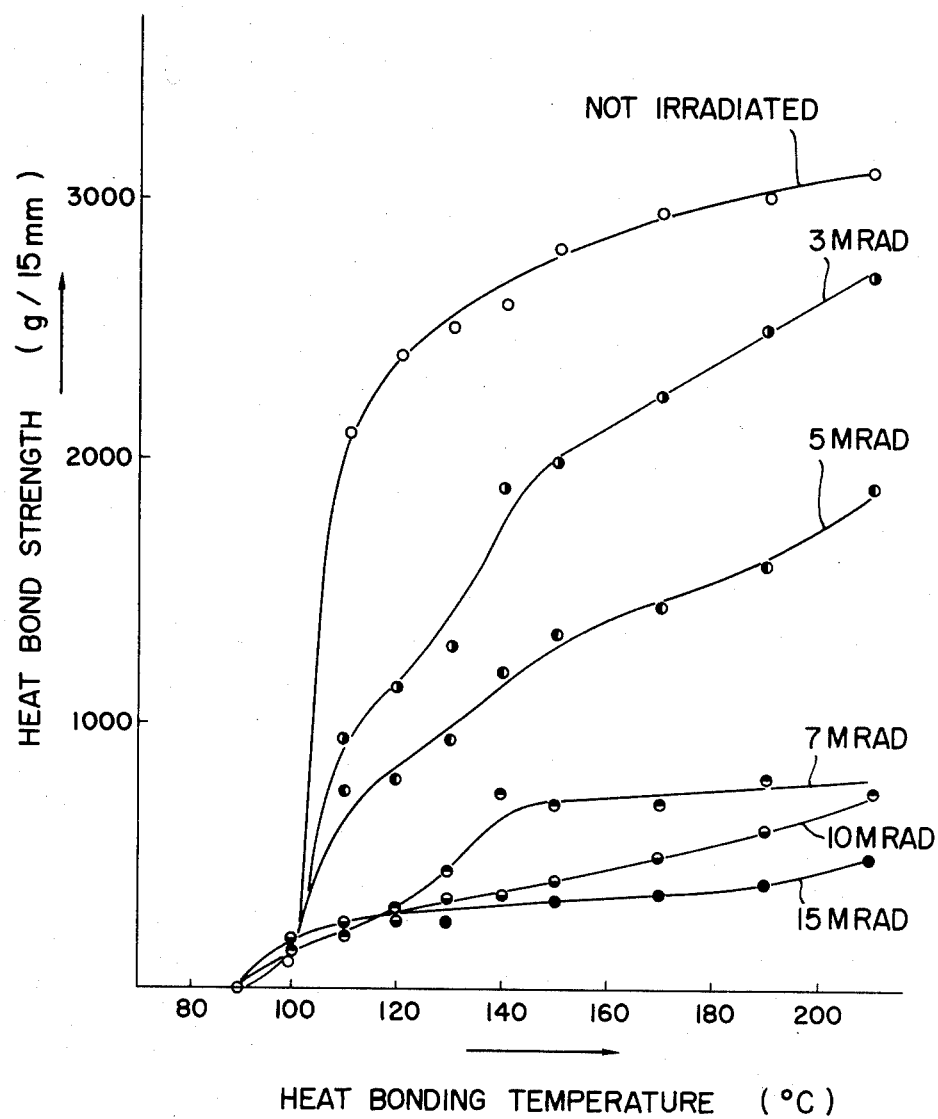

FIG. 4 indicates the same relationships of the sealed part of a sealed package produced in the same manner as in the bag container described above with reference to FIG. 3 except that the low-density polyethylene films on both sides of the sealed part were irradiated with the same quantity of ionizing radiation prior to forming of the sealed part.

Figure 5:
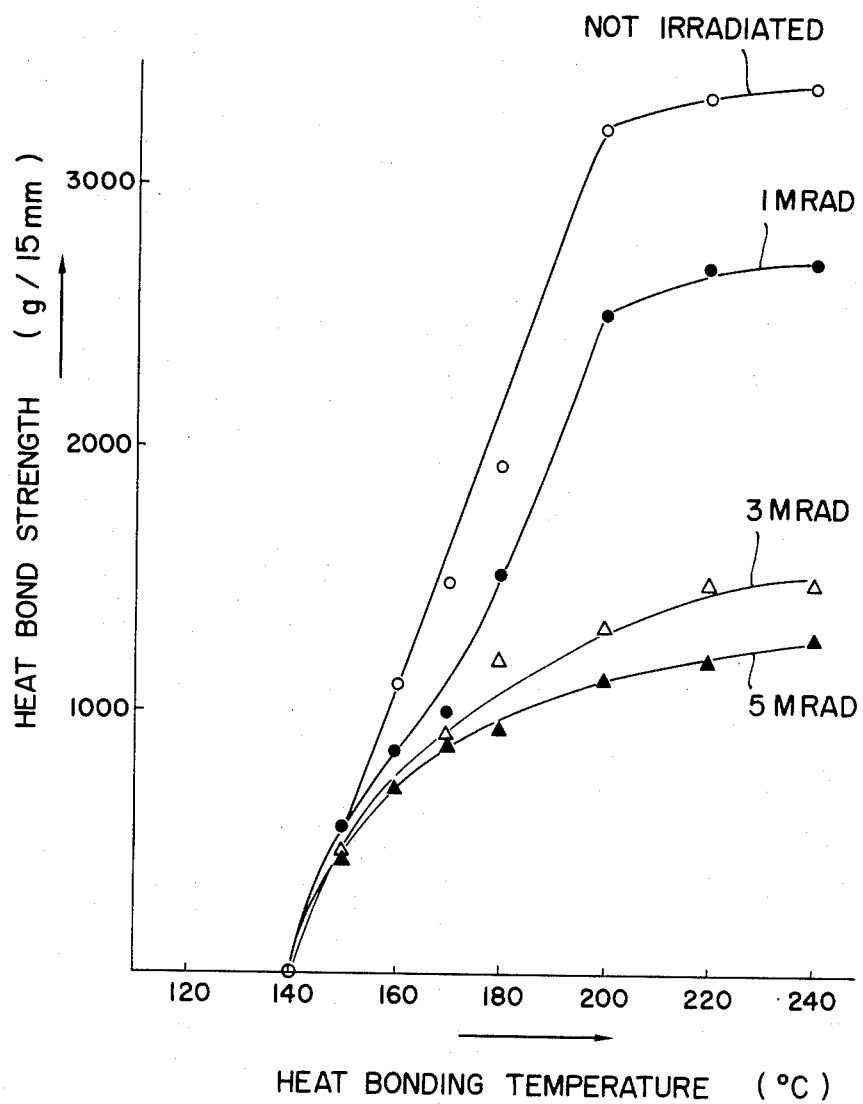

FIG. 5 also indicates the same relationships as mentioned above in the case of a sealed part produced by bonding together with an adhesive a polyethyleneterephthalate film of 12-micron thickness and a linear medium-density polyethylene film of 40-micron thickness to form a laminated film and heat bonding this laminated film with a polypropylene sheet of 0.7-mm thickness. The heat bonded part which is the sealed part was formed by heat bonding the linear medium-density polyethylene film in the laminated film with the polypropylene sheet, prior to which only the linear medium-density polyethylene film was irradiated with ionizing radiation rays.

In order to indicate more fully the nature and utility of this invention, the following specific example of practice thereof is set forth, it being understood that this example is presented as illustrative only and is not intended to limit the scope of this invention.

EXAMPLE

On a polyvinyl chloride sheet of 0.1-mm thickness, a low-density polyethylene layer of 30-$\mu$m thickness was formed by the extrusion coating method to obtain a compositeسheet. This composite sheet was then irradiated with ionizing radiation rays of an acceleration voltage of 175 KV and 5 Mrad, and a composite sheet with a crosslinked structure introduced into the low-density polyethylene thereof was obtained.

Next, with this composite sheet as a structural material, a box-shaped container with an open top and a flange of 5-mm width around the rim of the open top was formed with the low-density polyethylene layer surface on the inner side in a vacuum forming machine. This container was of a length of 50 mm, a width of 6 mm, and a depth of 5 mm.

Separately, on a sheet of high-quality paper of a basis weight of 64 grams/m$^2$, a dispersion containing an ionomer as the principal ingredient was applied as a coating in a quantity of 10 grams/m$^2$ to prepare a paper having an effective micropore diameter adjusted to the order of 0.2 to 0.3 $\mu$m. Then, on the surface coated with the dispersion of the paper thus obtained, a sheet of ionomer film having holes of 1-mm diameter over its entire surface with a distribution of 42 holes per square cm was laminated. The laminated sheet thus obtained was passed between hot rolls heated to 130° C. thereby to obtain a sheet of composite paper comprising paper and thermoplastic resin film having fine holes in bonded state. The gas permeability of this composite paper was measured by means of a Gurley type gas permeability tester and was found to be 700 sec/100 cc, whereby it was confirmed that the permeability with respect to gases for sterilization was ample.

Then, after hypodermic needles were packed in the aforementioned box-shaped container, the open top part of the container was covered with the above described composite paper with its thermoplastic resin film side on the inner side. This thermoplastic resin film and the upper surface of the flange part of the box-shaped container in contact with each other were heat bonded by heating to a temperature of 150° C. for 1 second. Thus, a sealed package containing a medical product constituting one embodiment of this invention and comprising, as the packaging structure, side walls and bottom made of the composite sheet of vinyl chloride sheet and low-density polyethylene layer and the upper cover wall made of the composite paper was obtained.

This sealed package was subjected to sterilization treatment with ethylene oxide gas, and then the bond strength of its sealed part was measured and found to be 600 g/20-mm width. It was also found that, at the time of unsealing, there was no tearing of the paper at the sealed part and no scattering whatsoever of paper dust, and a clean and neat unsealed part was formed. Moreover, the hypodermic needles, which had been the seal-packaged articles, were found to be in a perfectly sterile state.

As described above, either of the top cover of the container structure of the readily unsealable package and the side walls and bottom structure, or both are a multilayer structure comprising an inner wall layer of a thermoplastic resin having minute through holes and an outer wall layer laminated with the inner wall layer and possessing the characteristic of being permeable to gases but being impervious to microorganisms. Accordingly, this construction has the advantageous feature of making possible sterilization of the sealed article by gas sterilization, which is being used most widely.

Furthermore, the sealed part formed by heat bonding in the readily unsealable package of this invention is formed in exactly the same manner as sealed parts sealed by the conventional heat bonding method without using any special heat bonding conditions whatsoever. Therefore, the operation of forming the sealed part is easily accomplished. Moreover, the bond strength of the sealed part can be controlled in accordance with the size of the packaged commodity and its weight by merely varying the quantity of irradiation with ionizing radiation rays to which the thermoplastic resin layer having a polyethylene chain, which is directly related to the formation of the sealed part, is subjected. Thus, readily unsealable packages for medical supplies having specific heat bond strengths selected from a wide range thereof can be produced to meet specific respective needs.

It has been mentioned hereinbefore that when the sealed package of this invention is unsealed, there is no formation and scattering of paper dust and the resulting opening is neat and clean. This is because, although the package is unsealed by a pulling apart action, the separation of the joined parts is a separation at the interfaces of the mutually heat bonded thermoplastic resin layers. Thus, a very desirable unsealed surface from the standpoint of sanitation, which is most important for a package for medical supplies, and from the point of view of aesthetic value can be obtained.

What we claim is:

1. A container structure for packaging a commodity in a sterile sealed state to produce a readily unsealable sealed package of the commodity, said container structure comprising a first wall part and a second wall part which are heat bonded together along respective sealing portions, thereby forming an interface between the first and second wall parts, said sealing portions being formed from thermoplastic resin layers having a polyethylene chain, at least one wall part of the first and second wall parts being a laminated multilayer structure comprising a thermoplastic resin inner wall layer provided with a plurality of minute through holes and a paper outer wall layer laminated to the inner wall layer, said paper outer wall layer being permeable to gases but being impervious to microorganisms, the thermoplastic resin layer of at least one of said sealing portions being subjected to irradiation with ionizing radiation rays to introduce thereinto a crosslinked structure, said irradiation occurring prior to heat bonding in an amount sufficient to control the heat bonding strength between the first wall part and the second wall part such that the first wall part can be pulled apart from the second wall part at the interface therebetween.

2. A container structure according to claim 1, wherein said container has a substantially bag-like shape.

3. A container structure according to claim 1, wherein said container has a shape of a closable and sealable, three-dimensional vessel of substantially rigid character.

4. A container structure according to claim 1, wherein said container is adapted particularly for seal packaging medical supplies in a sterile state.

5. A container structure according to claim 1, wherein the first wall part is a laminated structure comprising an inner wall layer made of a thermoplastic resin and provided with a plurality of minute through holes and an outer wall layer laminated to the inner wall layer and made of a paper material which is permeable to gases but impervious to microorganisms, and the second wall part is a laminated structure comprising an inner wall layer of a thermoplastic resin and an outer wall layer of an aluminum sheet.

6. A container structure according to claim 1, wherein each of said thermoplastic resin layers comprises a member selected from the group consisting of polyethylenes, ethylene-vinyl acetate copolymers, ethylenecarboxylic acid copolymers, ethylene-α. olefin copolymers, propylene, polyvinyl chloride, and polystyrenes.

7. A readily unsealable sealed package comprising a sterile commodity and a container structure containing the commodity in a sterile sealed state and having first and second wall parts heat bonded together along respective sealing portions, thereby forming an interface between the first and second wall parts, said sealing portions being formed from thermoplastic resin layers having a polyethylene chain, at least one wall part of the first and second wall parts being a laminated multilayer structure comprising a thermoplastic resin inner wall layer provided with a plurality of minute through holes and a paper outer layer laminated to the inner wall layer, said paper outer wall layer being permeable to gases but being impervious to microorganisms, the thermoplastic resin layer of at least one of said sealing portions having been subjected to irradiation with ionizing radiation rays to introduce thereinto a crosslinked structure, said irradiation occurring prior to heat bonding in an amount sufficient to control the heat bonding strength between the first wall part and the second wall part such that the first wall part can be pulled apart from the second wall part at the interface therebetween.

8. A method of producing a container structure for packaging a commodity in a sterile sealed state to produce a readily unsealable sealed package of the commodity, which method comprises forming first and second wall parts having respective sealing portions, thereby forming an interface between the first and second wall parts, said sealing portions being formed from thermoplastic resin layers of the first and second wall parts having formed therein a plurality of minute through holes in an inner wall layer of a thermoplastic resin, preparing an outer wall layer of a paper material which is permeable to gases but impervious to microorganisms, and laminating the inner and outer wall layers, thereby forming a laminated multilayer structure to constitute said at least one wall part and irradiating with ionizing radiation rays at least one of said sealing portions to introduce thereinto a crosslinked structure, said irradiation occurring prior to heat bonding in an amount sufficient to control the heat bonding strength between the first wall part and the second wall part such that the first wall part can be pulled apart from the second wall part at the interface therebetween, and heat bonding the sealing portions together to form a sealed container structure.

9. A method of producing a readily unsealable sealed package of a commodity in a sterile state, which method comprises: forming first and second container wall parts having respective sealing portions, thereby forming an interface between the first and second wall parts, said sealing portions being formed from thermoplastic resin layers having a polyethylene chain, at least one wall part of the first and second wall parts having a plurality of minute through holes in an inner wall layer of a thermoplastic resin, preparing an outer wall layer of a paper material which is permeable to gases but impervious to microorganisms, and laminating the inner and outer wall layers to form a laminated multilayer structure to constitute said at least one wall part and irradiating with ionizing radiation rays at least one of said sealing portions to introduce thereinto a crosslinked structure, said irradiation occurring prior to heat bonding in an amount sufficient to control the heat bonding strength between the first wall part and the second wall part such that the first wall part can be pulled apart from the second wall part at the interface therebetween; placing the commodity between the first and second wall parts; joining and sealing the sealing portions of the wall parts by heat bonding to form a sealed container structure enclosing the commodity; and sterilizing the commodity thus enclosed with a sterilizing steam.

10. A container structure for packing a commodity in a sterile sealed state to produce a readily unsealable sealed package of the commodity, said container structure comprising a first wall part and a second wall part which are heat bonded together along respective sealing portions, thereby forming an interface between the first and second wall parts, said sealing portions being formed from thermoplastic resin layers having a polyethylene chain, the thermoplastic resin layer of at least one of said sealing portions being subjected to irradiation with ionizing radiation rays to introduce thereinto a crosslinked structure, said irradiation occurring prior to heat bonding in an amount sufficient to control the heat bonding strength between the first wall part and the second wall part such that the first wall part can be pulled apart from the second wall part at the interface therebetween.

* * * * *